United States Patent [19]
Kaufmann et al.

[11] Patent Number: 5,318,568
[45] Date of Patent: Jun. 7, 1994

[54] INFLATABLE BLANKET AND NOZZLE THEREFOR

[75] Inventors: Rick J. Kaufmann, Los Gatos; Rick E. Emerson; Robert L. Lathrop, Jr., both of San Jose, all of Calif.

[73] Assignee: Advanced Warming Systems, Inc., Lubbock, Tex.

[21] Appl. No.: 793,009

[22] Filed: Nov. 15, 1991

[51] Int. Cl.⁵ .............................................. A61F 7/00
[52] U.S. Cl. ..................................... 607/107; 285/320
[58] Field of Search ............... 128/400, 399, 402, 403; 165/46; 285/244, 320, 317; 5/482

[56] References Cited

U.S. PATENT DOCUMENTS

| | | | |
|---|---|---|---|
| 2,512,559 | 6/1950 | Williams | 5/482 |
| 2,520,215 | 8/1950 | Kerr | 285/320 |
| 2,528,369 | 10/1950 | Jensen | 285/320 |
| 3,295,869 | 1/1967 | Chambers | 285/320 |
| 3,700,112 | 10/1972 | Maeshiba | 285/317 |
| 4,444,419 | 4/1984 | Maeshiba | 285/320 |
| 4,777,802 | 10/1988 | Feher | 5/482 |
| 4,867,230 | 9/1989 | Voss | 165/46 |
| 5,078,429 | 1/1992 | Braut | 285/320 |

OTHER PUBLICATIONS

"The WarmAir ® System", Cincinnati Sub-Zero Products, Inc. (May 1991).

Primary Examiner—Mark S. Graham
Attorney, Agent, or Firm—Mason, Fenwick, & Lawrence

[57] ABSTRACT

Hypothermia therapy apparatus comprises an inflatable blanket having a cavity therein, and a neck extending outwardly of the perimeter of the blanket body, the interior of the neck being in communication with the cavity. A nozzle is also provided, the forward portion of the nozzle being receivable in the outer end of the neck, and the rearward portion of the nozzle is connectable with a source of air. The nozzle includes an engagement mechanism for engaging at least a portion of the exterior surface of the neck. The engagement mechanism comprises a spring clip normally biased in the closed position and selectively openable to receive a portion of the neck thereunder. The forward portion of the nozzle is frusto-conical to facilitate insertion into the open end of the neck, and the neck is dimensioned to loosely engage the intermediate portion of the nozzle. A connector is provided for removably connecting an air hose to the rearward portion of the nozzle. The nozzle and the connector are rotatable relative to each other about their longitudinal axes, to prevent twisting of the blanket when the nozzle is attached to the neck.

15 Claims, 3 Drawing Sheets

5,318,568

INFLATABLE BLANKET AND NOZZLE THEREFOR

BACKGROUND OF THE INVENTION

1. Field of the Invention

The present invention relates to hypothermia therapy apparatus comprising an inflatable blanket and a nozzle therefor. More specifically, the invention relates to an inflatable blanket and a nozzle provided with an interengagement mechanism.

2. Related Art

In hospitals today, 70% of all post-operative patients are hypothermic. This translates to 14 million people each year. Hypothermia is probably the most common, yet ignored, complication of surgery, and side effects can be serious.

Patients come into surgery in a state of normothermia, but core body temperature decreases during surgery, due to the effects of anesthesia, the air conditioning in the operating room, and cold blood, intravenous, and irrigating fluids. As a result of hypothermia, patients, especially the elderly, need longer stays in the recovery room. Most critical care patients also are cold and hypothermic. Further, core hypothermia is the cause of shivering in O-B patients following epidural and spinal anesthesia. Many post-surgical patients have vivid memories of the cold; they shiver. Some develop several coagulapathies, and arrhythmia can occur.

The goal of warming therapy is to keep patients normo-thermic, but nearly all current methods, including infrared lamps, cotton blankets, and warm water mattresses, are ineffective. Scientific studies have shown that patients actually lose heat with infrared lamps, cotton blankets, and warm water mattresses.

Forced air convection is the only therapy that actually makes the patient warmer. Present forced air convection therapy systems employ an inflatable blanket or tube which is connected to a hose that delivers warm forced air. However, due to the need for a system which is both inexpensive and disposable, present forced air convection systems use paper and plastic tubes and blankets. The receptacle for the heater hose generally comprises a hole in the tube or blanket which is reinforced by a cardboard plate having a similarly dimensioned hole therethrough. These holes have a diameter slightly smaller than that of the heater hose, and are provided at their perimeters with radial slits, so that they will bend to matingly engage the heater hose. However, pressure from the flowing air and movement of the hose in the receptacle quickly weakens the engagement between the receptacle and the hose. This results in leakage of the warm air, reducing the effectiveness of the forced air convection system, and ultimately in disengagement of the hose from the receptacle. When this occurs, the warming blanket or tube must be replaced. It is the solution of these and other problems to which the present invention is directed.

SUMMARY OF THE INVENTION

It is a primary object of the present invention to provide a hypothermia therapy apparatus comprising an inflatable blanket and a nozzle therefor wherein the blanket and the nozzle remain interengaged until disengaged by an operator.

It is another object of the present invention to provide an inflatable blanket and a nozzle therefor wherein the interengagement between the two does not loosen over time through use It is still another object of the present invention to provide an inflatable blanket and a nozzle therefor wherein the blanket can be attached directly to the nozzle without additional attachment components.

These and other objects of the invention are achieved through the provision of hypothermia therapy apparatus comprising a blanket having a cavity therein for inflation of the blanket, and a neck extending outwardly of the perimeter, the interior of the neck being in communication with the cavity. The blanket is made of a flexible material, the neck being selectively expandable and collapsible between open and closed positions. The neck has an open outer end for receiving the forward portion of a nozzle. The rearward portion of the nozzle is connectable with a source of ambient or heated air. The nozzle includes an engagement mechanism for engaging at least a portion of the exterior surface of the neck.

The forward portion of the nozzle is frusto-conical to facilitate insertion into the open end of the neck, and the neck is dimensioned to loosely engage the intermediate portion of the nozzle.

In one aspect of the invention, the neck includes tabs at the open end to facilitate opening the neck and pulling it over the forward portion of the nozzle.

In another aspect of the invention, the engagement mechanism comprises a spring clip normally biased in the closed position and selectively openable to receive a portion of the neck thereunder.

In still another aspect of the invention, a connector is provided for removably connecting an air hose to the rearward portion of the nozzle. The nozzle and the connector are rotatable relative to each other about their longitudinal axes, to prevent twisting of the blanket when the nozzle is attached to the neck.

BRIEF DESCRIPTION OF THE DRAWINGS

The invention is better understood by reading the following detailed description of the preferred embodiments with reference to the accompanying drawing figures, in which like reference numerals refer to like elements throughout, and in which.

DETAILED DESCRIPTION OF THE PREFERRED EMBODIMENTS

Figure 1:
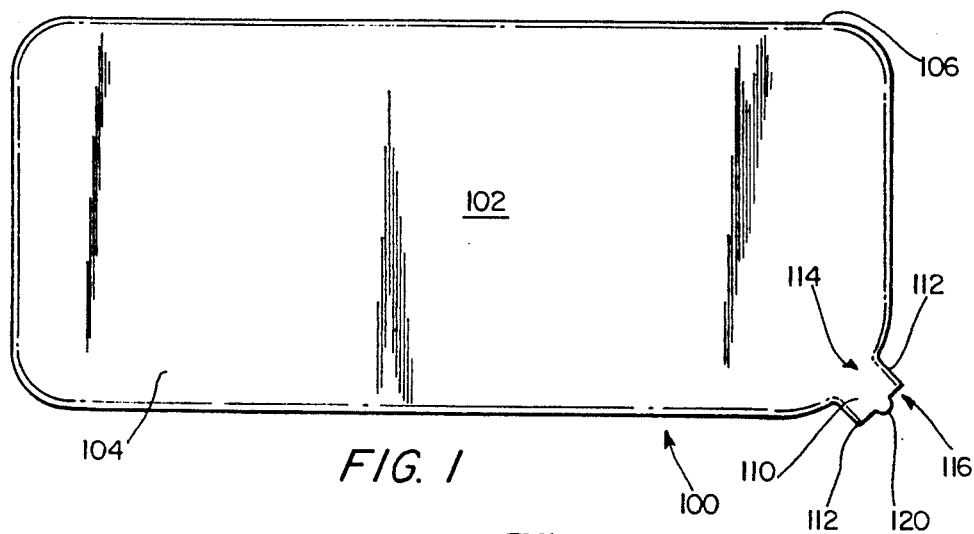
FIG. 1 is a top plan view of an inflatable blanket in accordance with the present invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

Figure 2:
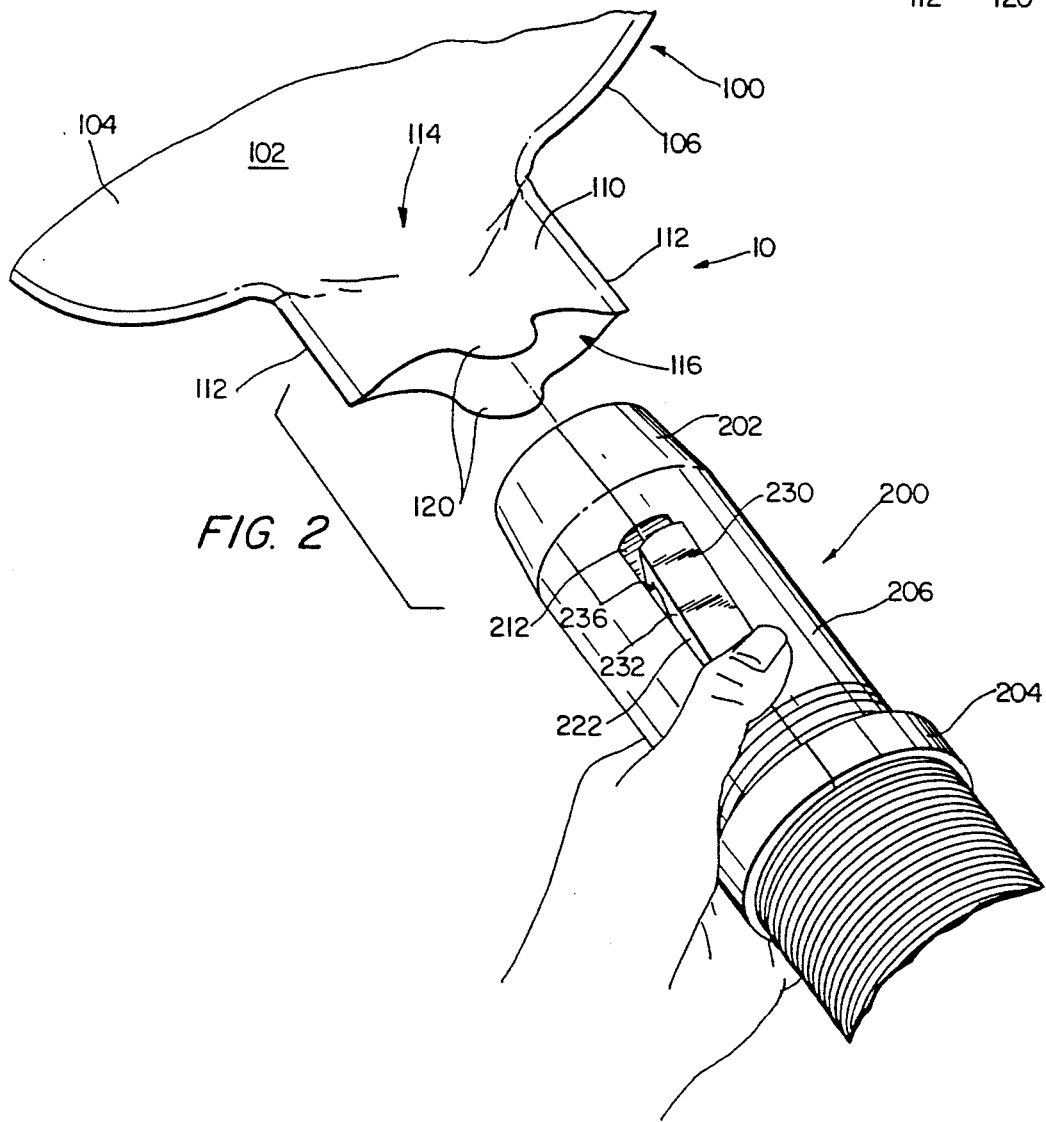
FIG. 2 is a perspective view of a nozzle in accordance with the present invention prior to insertion into the neck of the blanket of FIG. 1.
Figure 2A:
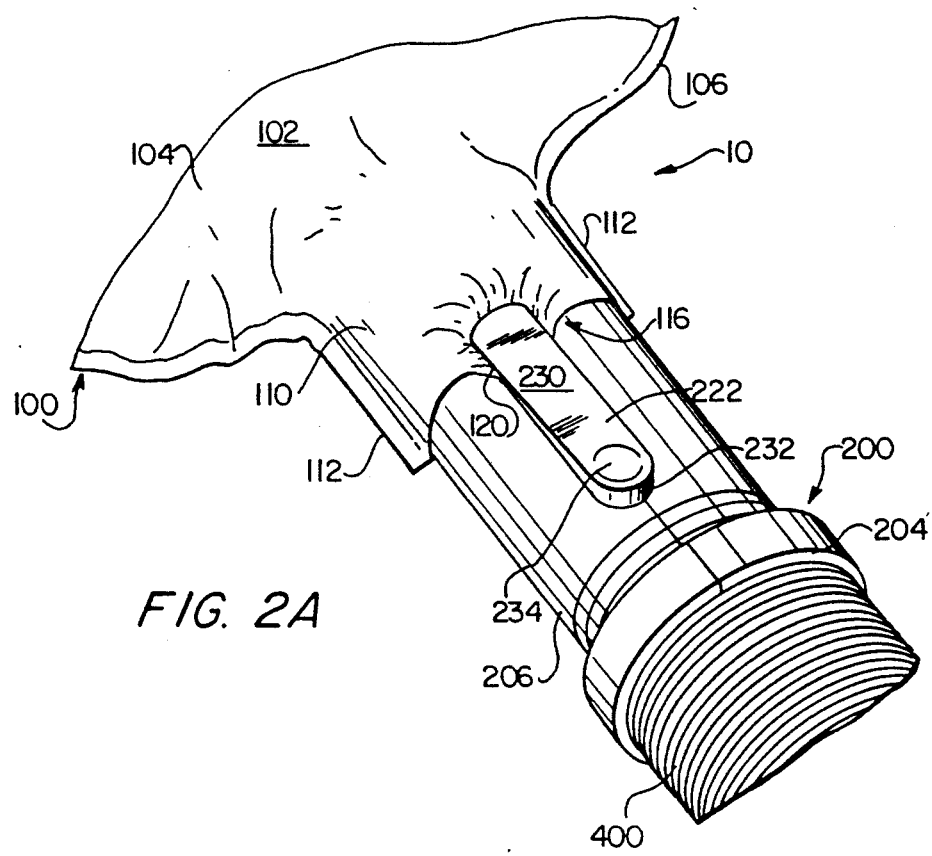
FIG. 2a is a perspective view of the nozzle of FIG. 2 inserted into the neck of the blanket.

Referring now to FIGS. 2 and 2A, there is shown hypothermia therapy apparatus 10 in accordance with the present invention comprising an inflatable blanket 100 and a nozzle 200 therefor. As best shown in FIG. 1, blanket 100 comprises first and second sheets 102, which are mirror images of each other. Each of sheets 102 includes a body portion 104 having a perimeter 106. A neck portion 110 extends outwardly of perimeter 106 and includes closed sides 112, an open inner end 114 co-extensive with perimeter 106, and an open outer end 116 opposite inner end 114. Tabs 120 extend outwardly from neck portion 110 at open outer end 116, for a purpose to be described hereinafter.

Sheets 102 are made of a flexible material suitable for hospital use, such as paper with a polyethylene plastic liner. Perimeters 106 and sides 112 are joined together, for example by ultrasonic welding, such that the interior faces of sheets 102 define within perimeters 106 a cavity for inflation of blanket 100 and define between sides 112 a neck interior in communication with the cavity.

Figure 3:
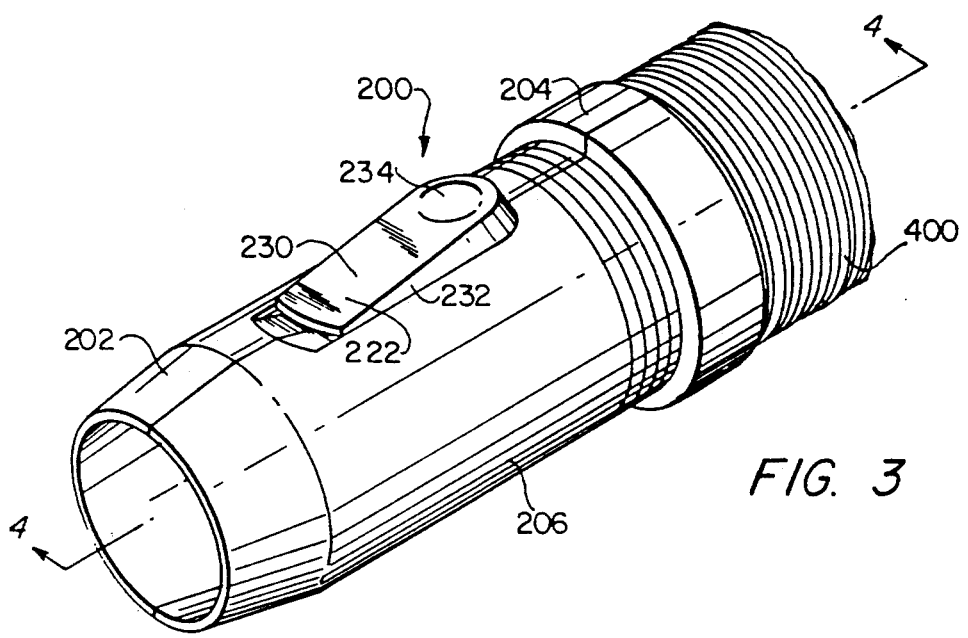
FIG. 3 is a perspective view of the nozzle of FIG. 2.
Figure 4:
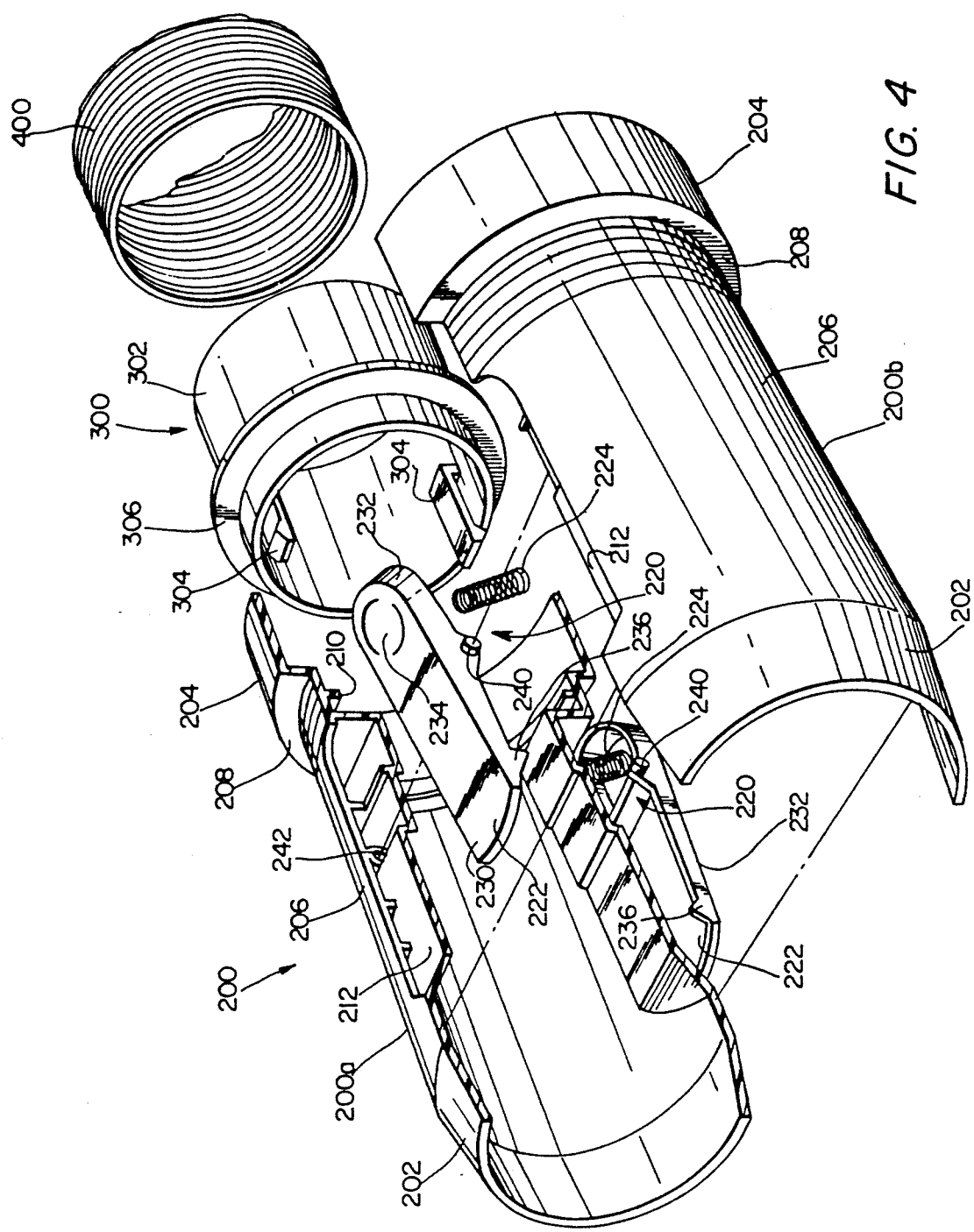
FIG. 4 is a perspective view of the nozzle of FIG. 2, exploded along line 4—4 of FIG. 3.

Referring now to FIGS. 2–4, nozzle 200 includes a tapered or frusto-conical forward portion 202, a substantially cylindrical rearward portion 204, and a substantially cylindrical intermediate portion 206 intermediate forward and rearward portions 202 and 204.

As best seen in FIG. 4, the inner and outer diameters of rearward portion 204 are larger than the inner and outer diameters of intermediate portion 206, thus resulting in the formation of a shoulder 208 at the junction between rearward portion 204 and intermediate portion 206. An annular ridge 210 is provided on the inner surface of intermediate portion 206 adjacent rearward portion 204, for a purpose to be described hereinafter.

Longitudinal recesses 212 are provided at opposed positions in intermediate portion 206 for receiving spring clip mechanisms 220. Each spring clip mechanism 220 comprises a clip 222 having a coil spring 224 positioned under its rearward end for normally biasing the forward end of clip 222 in the closed position.

Each clip 222 includes a top wall 230 and a sidewall 232. Top wall 230 is provided with a depression 234 therein for accommodating the thumb or finger of the system operator. Extensions 236 project downwardly from the forward end of sidewall 232 for cinching neck portion 110 of blanket 100 against the outer surface of nozzle 200. Pivot pins 240 project outwardly from the central portions of sidewalls 232 for engaging mating apertures 242 formed in the sides of depressions 234, for permitting pivoting movement of clip 222 about an axis through pins 240.

Clips 222 function both to retain neck portion 110 on nozzle 200 and to create a seal against air leakage, by causing the inside circumference of neck portion 110 to conform to the shape of the circumference of nozzle 200.

As best shown in FIG. 4, apparatus 10 further includes a connector 300 for connecting nozzle 200 to a hose 400. Connector 300 comprises a substantially cylindrical body 302 having opposed resilient L-shaped fingers 304 extending from the inner surface thereof for engaging annular ridge 210 of nozzle 200. The resilience of fingers 304 permits them to be snap fit over ridge 210 for connection of connector 300 to nozzle 200; and permits fingers 304 to retract over ridge 210 when connector 300 is pulled rearwardly away from nozzle 200, to disconnect connector 300 from nozzle 200. Also, fingers 304 of connector 300 are slidable circumferentially around ridge 210, for a purposed to be described hereinafter.

Hose 400 is inserted over the rearward end of connector 300, an annular ridge 306 on the outer surface of connector 300 acting as a stop against further forward movement of hose 400. Hose 400 can be secured to connector 300 by a conventional adhesive. Further, a layer of foam (not shown) can be secured to the inner surface of connector 300, also by means of a conventional adhesive, to provide a degree of sound insulation. Hose 400 is connectable at its other end to a source of heated or ambient air.

Preferably, nozzle 200, including clips 222, is formed of a light-weight plastic. Further, except for clips 200, nozzle 200 is formed in two longitudinally-symmetric sections 200a and 200b, forward, rearward, and intermediate portions 202, 204, and 206 of each section being formed unitarily.

Sections 200a and 200b are made by molding using a plastic which can be ultrasonically welded, while clips 222 are made by molding using a plastic which is not capable of being ultrasonically welded. Thus, sections 200a and 200b can be assembled together with clips 222 and subjected to ultrasonic energy, so that sections 200a and 200b will be welded together to retain clips 222 in recesses 212, clips 222 remaining free to pivot in recesses 212. As will be appreciated by those of skill in the art, sections 200a and 200b can also be joined together using a conventional adhesive, thus permitting them to be made of a material which is not capable of being ultrasonically welded.

Neck portion of 110 of blanket 100 is dimensioned to loosely engage intermediate portion 206 of nozzle 200. This looseness is critical to the ease of insertion of nozzle 200 into neck portion 110 by the operator. In use, the operator of the system opens neck portion 110, and using tabs 120, pulls neck portion 110 over forward portion 202 of nozzle 200. The frusto-conical configuration of forward portion 202 facilitates insertion of nozzle 200 into neck portion 110.

By pressing down on clips 222 at depressions 234, the system operator can open clips 222 to engage neck portion thereunder. Longitudinal recesses 212 serve the function of increasing the outer perimeter of nozzle 200. The excess material in neck portion 11? thus is taken up by longitudinal recesses 212 when neck portion 110 is inserted between longitudinal recesses 212 and clips 222 and clips 22 are closed. Clips 222 cinch neck portion 110 within recesses 212 and against intermediate portion 206 of nozzle 200, thereby forming a substantially air-tight engagement between neck portion 110 of blanket 100 and nozzle 200. Thus, nozzle 200 eliminates all requirements for extra receptacles, seals, etc. on blanket 100, which in turn minimizes the cost of blanket 100.

Nozzle 200 is connected to hose 400 using connector 300 as previously described. Because fingers 304 of connector 300 are slidable around ridge 210, nozzle 200 and connector 300 are rotatable relative to each other about their longitudinal axes, thus preventing twisting of blanket 100 when nozzle 200 is attached to neck portion 110. Also, because nozzle 200 can be disconnected from connector 300, it can be easily cleaned or sterilized as required.

Hose 400 preferably is a conventional, light-weight, fixable hose, such as TIGERFLEX EXTENDO-DUCT ® (polypropylene/wire reinforced) ducting hose made by Kuriyama of America, Inc. of Elkgrove Village, Ill. This type of hose is contractible and expandable in the axial direction, as well as being fixable, so that it can be arranged in any convenient configuration with respect to blanket 100 and nozzle 200 at one end and the source of air at the other end.

Modifications and variations of the above-described embodiments of the present invention are possible, as appreciated by those skilled in the art in light of the above teachings. For example, the nozzle can be scaled in size to accommodate other blanket neck or hose duct sizes.

It is therefore to be understood that, within the scope of the appended claims and their equivalents, the invention may be practiced otherwise than as specifically described.

What is claimed is:

1. Hypothermia therapy apparatus comprising:
    a blanket having a body portion and a neck, said body portion having a cavity therein for inflation of said blanket and a perimeter, and said neck extending outwardly of said perimeter and having an interior surface defining an interior in communication with said cavity, an open outer end, and an exterior surface, said blanket being made of a flexible material and said neck being selectively expandable and collapsible between open and closed positions; and
    a nozzle having a forward portion, a rearward portion, an intermediate portion intermediate said forward and rearward portions, and engagement means located at said intermediate portion for engaging at least a portion of said exterior surface of said neck, said intermediate portion including a pair of longitudinal recesses, said engagement means being received within said longitudinal recesses, said forward portion and at least a portion of said intermediate portion being insertable through said open outer end into said interior of said neck, and said rearward portion being connectable with a source of air.

2. The apparatus of claim 1, wherein said forward portion of said nozzle is frusto-conical.

3. The apparatus of claim 1, wherein said forward portion extends forwardly of said engagement means and said rearward portion extends rearwardly of said engagement means.

4. The apparatus of claim 1, wherein said intermediate portion of said nozzle is substantially cylindrical.

5. The apparatus of claim 1, wherein said neck is dimensioned to loosely engage said intermediate portion of said nozzle; and
    wherein said engagement means comprises a pair of clips received within said longitudinal recesses, said clips being normally biased in a closed position and selectively openable to receive a portion of said neck thereunder within said longitudinal recesses to tightly engage said neck against said nozzle to create a substantially air-tight seal between said neck and said nozzle.

6. The apparatus of claim 5, wherein each of said clip mechanisms comprises:
    a clip having a forward end and a rearward end and being pivotably mounted within one of said longitudinal recesses; and
    biasing means positioned at said rearward end of said clip for normally biasing said forward end in the closed position.

7. The apparatus of claim 1, wherein said neck is dimensioned to loosely engage said intermediate portion of said nozzle, and wherein said engagement means tightly engages said neck within said recesses to create a substantially air-tight seal between said neck and said nozzle.

8. The apparatus of claim 1, wherein said neck includes a pair of opposed tabs extending outwardly from said open end for opening said neck and pulling said neck over said forward portion of said nozzle.

9. The apparatus of claim 1, further comprising connector means for removably connecting an air hose to said rearward portion of said nozzle.

10. The apparatus of claim 9, wherein said nozzle and said connector means are freely rotatable relative to each other about their longitudinal axes.

11. The apparatus of claim 10, wherein said nozzle at said rearward portion includes an annular ridge and wherein said connector means includes at least two resilient fingers releasably engaging said ridge, said fingers being slidable around said ridge.

12. The apparatus of claim 9, wherein said nozzle and said connector means are freely rotatable relative to each other about their longitudinal axes without substantial relative axial motion.

13. The apparatus of claim 11, wherein said annular ridge is formed in the inner surface of said rearward portion of said nozzle, and said finger means are positioned on the inner surface of said connector means.

14. Hypothermia therapy apparatus comprising:
    a blanket having a body portion and a neck, said body portion having a cavity therein for inflation of said blanket and a perimeter, and said neck extending outwardly of said perimeter and having an interior surface defining an interior in communication with said cavity, an open outer end, and an exterior surface, said blanket being made of a flexible material and said neck being selectively expandable and collapsible between open and closed positions;
    a nozzle having a frusto-conical forward portion for insertion into said neck, a rearward portion, a substantially cylindrical intermediate portion intermediate said forward and rearward portions and including a pair of longitudinal recesses, and a pair of clip mechanism received within said longitudinal recesses, said forward and intermediate portions being insertable through said open outer end into said interior of said neck, each of said clip mechanisms comprising a clip having a forward end and a rearward end and being pivotably mounted within one of said longitudinal recesses and biasing means positioned at said rearward end of said clip for normally biasing said forward end in the closed position for engaging at least a portion of said exterior surface of said neck when said forward and intermediate portions are inserted into said interior of said neck, said forward portion extending forwardly of said clip mechanisms and said longitudinal recesses, said rearward portion extending rearwardly of said clip mechanisms and said longitudinal recesses; and
    connector means for removably connecting an air hose to said rearward portion of said nozzle.

15. The apparatus of claim 14, wherein said nozzle and said connector means are freely rotatable relative to each other about their longitudinal axes without substantial relative axial motion; and
    wherein said nozzle at said rearward portion includes an annular ridge formed on the inner surface thereof, and wherein said connector means includes at least two resilient fingers releasably engaging said ridge, said fingers being slidable around said ridge.

* * * * *